US007279183B2

(12) United States Patent
Kaul et al.

(10) Patent No.: US 7,279,183 B2
(45) Date of Patent: *Oct. 9, 2007

(54) METHOD OF REDUCING THROMBOSIS AND COMPLICATIONS AFTER ARTERIAL ANGIOPLASTY USING STENT COATED WITH MAGNESIUM-BASED COMPOUND

(75) Inventors: Sanjay Kaul, Northridge, CA (US); Prediman K. Shah, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 328 days.

This patent is subject to a terminal disclaimer.

(21) Appl. No.: 10/746,048

(22) Filed: Dec. 24, 2003

(65) Prior Publication Data

US 2004/0138739 A1    Jul. 15, 2004

Related U.S. Application Data

(62) Division of application No. 09/908,342, filed on Jul. 18, 2001, now Pat. No. 6,692,772.

(51) Int. Cl.
*A61K 33/06* (2006.01)
*A61K 33/08* (2006.01)
*A61K 33/12* (2006.01)
*A61K 33/14* (2006.01)
*A61K 33/42* (2006.01)
*A61P 9/14* (2006.01)
*A61P 43/00* (2006.01)
*A61P 41/00* (2006.01)
*A61F 2/06* (2006.01)

(52) U.S. Cl. ............... 424/601; 424/423; 424/681; 424/682; 424/683; 424/686; 424/692; 424/697; 424/709; 514/56; 514/822; 623/1.43; 623/921

(58) Field of Classification Search ............... 424/601, 424/681–683, 686, 688–689, 692, 697, 709, 424/423; 514/56, 822; 623/1.43, 921
See application file for complete search history.

(56) References Cited

U.S. PATENT DOCUMENTS

| | | | |
|---|---|---|---|
| 4,182,774 | A | 1/1980 | Welstead, Jr. et al. |
| 5,849,338 | A | 12/1998 | Richardson et al. |
| 6,042,849 | A | 3/2000 | Richardson et al. |
| 6,087,373 | A | 7/2000 | Coburn et al. |
| 6,100,297 | A | 8/2000 | Weglicki |
| 6,287,332 | B1 | 9/2001 | Bolz et al. |
| 6,692,772 | B2 * | 2/2004 | Kaul et al. ............... 424/601 |
| 6,709,379 | B1 * | 3/2004 | Brandau et al. ............... 600/3 |

FOREIGN PATENT DOCUMENTS

JP    2000210380    8/2000

WO    PCT/GB00/00690    8/2000

OTHER PUBLICATIONS

Carrozza, J.P. 'Thrombosis and Drug-eluting stents: should we be concerned? A Commentary.' [online]. Aug. 26, 2004, [retrieved on Apr. 28, 2006]. Retrieved from the Internet: <URL: http://www.cardiosource.com/ExpertOpinion/hottopics/article.asp?paperID =79 >.*

'Drug-Eluting Stents'. [online]. Apr. 3, 2006 [retrieved on Apr. 28, 2006]. Retrieved from the Internet: <URL: http://www.ptca.org/articles/desl.html >.*

Somberg, J. et al., "Late stent thrombosis: problem or not?" The American Journal of Cardiology, vol. 99(7), Apr. 2007, pp. 1020-1023.*

Hara, H. et al., "Role of stent design and coatings on restenosis and thrombosis," Advanced Drug Delivery Reviews, vol. 58, pp. 377-386 (2006).*

Medline abstract 2001681052 (2001).*

Medline abstract 2002088281 (2002).*

Medline abstract 2001408480 (2001).*

Rukshin, V., et al., "Intravenous Magnesium in Experimental Stent Thrombosis in Swine," Ateriorscler Thromb Vasc Biol. 21(9):1544-49 (Sep. 2001).

Gertz, D.S., et al., "Effect of Magnesium Sulfate on Thrombus Formation following Partial Arterial Constriction: Implications for Coronary Vasospasm," Magnesium. 6(5):225-35 (1987).

Claus, H-D., "Zur Frage de Wirksamkeit einer thromboembolieprophylaxe durch Magnesium bei der Kontakttherapie von Portio- und Korpuskarzinomen der Uterus mit Gammastrahlem," Strahlentherapie, 135(3):291-94 (Mar. 1968) (Abstract in English).

Ravn, H.B., et al., "Magnesium Inhibits Platelet Activity—Infusion Study in Healthy Volunteers," Thrombosis and Haemostasis. 75(6):939-44 (Jun. 1996).

www.americanheart.org, Angioplasty, Percutaneous Transluminal Coronary (PTCA), Mar. 23, 2001.

H.B. Ravn, et al., "Early Administration of Intravenous Magnesium Inhibits Arterial Thrombus Formation," Arteriosclerosis, Thrombosis, and Vascular Biology, vol. 17(12), 1997, pp. 3620-3625.

Michael Shechter et al., "Low intracellular magnesium levels promote platelet-dependent thrombosis in patients with coronary artery disease," American Heart Journal, 140:212-218 (Aug. 2000).

Vladimir Rukshin et al, "Intravenous Magnesium in Experimental Stent Thrombosis in Swine," Arteriosclerosis, Thrombosis and Vascular Biology, 21:1544-1549 (Sep. 2001).

(Continued)

*Primary Examiner*—John Pak
(74) *Attorney, Agent, or Firm*—Seth D. Levy; Davis Wright Tremaine LLP

(57) ABSTRACT

Treatment with magnesium produces a inhibition of acute stent thrombosis under high-shear flow conditions without any hemostatic or significant hemodynamic complications.

33 Claims, 6 Drawing Sheets

OTHER PUBLICATIONS

S.D. Gertz et al., "Effect of Magnesium Sulfate on Thrombus Formation Following Partial Arterial Constriction: Complications for Corornary Vasospasm," Magnesium, vol. 6, No. 5, pp. 225-235 (1987).

H-D Claus, "Zur Frage der Wirksamkeit einer Thromboembolieprophylaxe durch Magnesium bei der Kontakttherapie von Portio- und Korpuskarzinomen der Uterus mit Gammastrahlern," Strahlentherapie, vol. 135, No. 3, pp. 291-294 (1968).

H.B. Ravn et al., "Magnesium Inhibits Platelet Activity—an infusion study in healthy volunteers," Thrombosis and Haemostasis, vol. 75, No. 6, pp. 939-944 (1996).

Vladimir Rukshin et al, "Comparative Antithrombotic Effects of Magnesium Sulfate and the Platelet Glycoprotein IIb/IIIa Inhibitors Tirofiban and Eptifibatide in a Canine Model of Stent Thrombosis," Circulation, vol. 105, pp. 1970-1975 (2002).

* cited by examiner

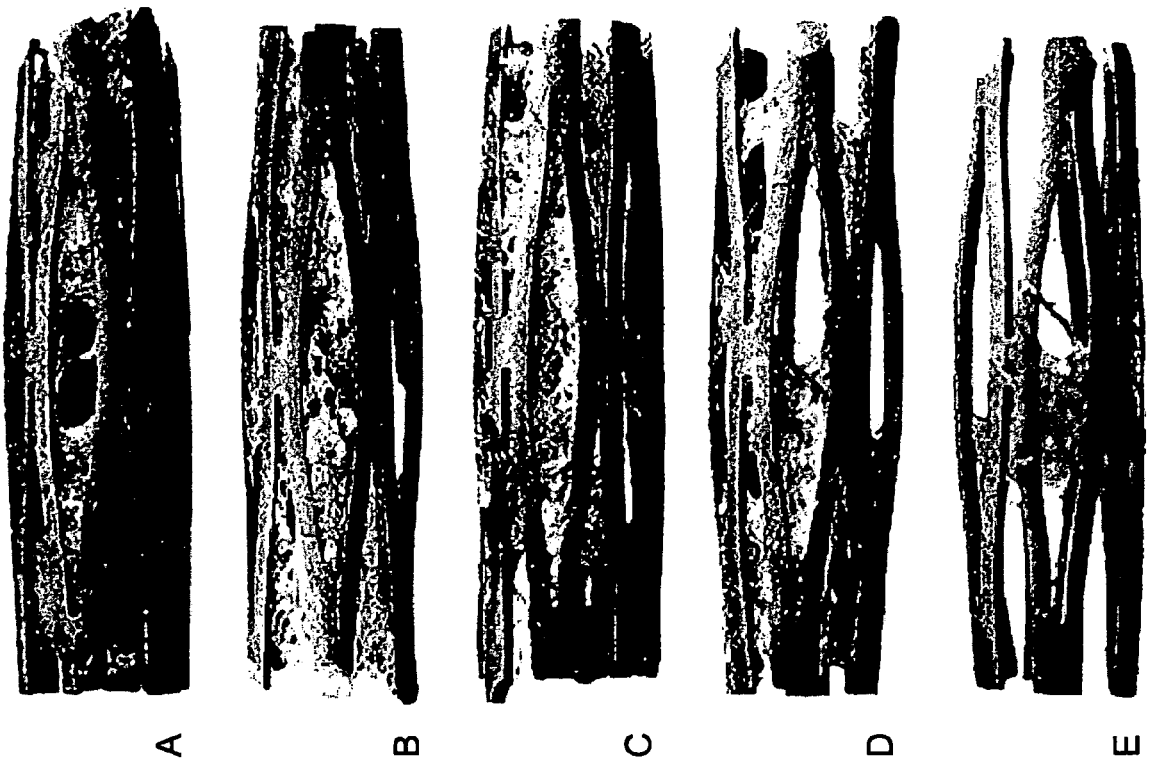

Reduction in Stent TW

| | |
|---|---|
| Baseline | — |
| Mg-Early | 42±21% |
| Mg-Late | 47±19% |
| Heparin | 48±16% |
| Heparin + Mg-Early | 67±12% |
| Heparin + Mg-Late | 86±8% |

Fig. 4

Values are mean±SD; n = 8-15 for Mg-early and Mg-late and 20-35 for the rest. *$P<.001$ vs. baseline. ANOVA

Effects on Platelet Function, Activated Clotting Time, and Serum Magnesium Level

| Intervention | Platelet aggregation (ohms$_{MAX}$) | Bleeding time (minutes) | ACT (seconds) | Serum Mg (mEq/L) |
|---|---|---|---|---|
| Baseline | 25±3 | 4.0±0.5 | 109±8 | 1.7±0.2 |
| Mg-Late alone | 22±3 | 4.5±0.5 | 104±5 | 3.7±0.6* |
| Heparin | 24±6 | 5.3±0.6* | 185±36* | — |
| Heparin + Mg-Early | 23±4 | 5.3±0.8* | 153±17* | 3.7±0.3* |
| Heparin + Mg-Late | 21±5 | 6.0±1* | 162±24* | 3.8±0.4* |

Fig. 5

Values are mean±SD; n = 8-9 for each variable. *P<0.01 vs. baseline. ANOVA

ACT = activated clotting time

METHOD OF REDUCING THROMBOSIS AND COMPLICATIONS AFTER ARTERIAL ANGIOPLASTY USING STENT COATED WITH MAGNESIUM-BASED COMPOUND

This application claims the benefit of priority under 35 U.S.C. §111 as a divisional of U.S. patent application Ser. No. 09/908,342, filed Jul. 18, 2001, now issued as U.S. Pat. No. 6,692,772, on Feb. 17, 2004.

BACKGROUND OF THE INVENTION

1. Field of the Invention

This invention relates to methods of treating thrombosis, and more particularly to the use of magnesium to prevent conditions such as in-stent thrombosis.

2. Discussion of the Related Art

Coronary artery disease is one of the country's largest health concerns. According to the American Heart Association, this disease affects 13.5 million Americans. Almost a million of these people have experienced heart attacks. Still others have experienced angina, undergone coronary artery bypass surgery and/or had heart transplants. Others in the later, or more severe, stages of coronary artery disease are in varying stages of congestive heart failure.

Coronary artery disease, which has been linked with the increase in cholesterol and saturated fat in our diets, is treatable. One main symptom of coronary artery disease is the deposit of these fatty materials alongside a vessel wall such as an arterial wall. This results in the progressive narrowing of the lumen, and arteriosclerosis. Such deposits may be treated through a procedure called angioplasty. During angioplasty, the doctor inserts a catheter into an artery, typically a groin artery, and maneuvers the catheter up through the artery until the catheter is positioned at the site of the narrowing or obstruction caused by plaque. The plaque may then be flattened by inflating a balloon located around the tip of the catheter. As the balloon expands, it compresses the fatty deposits against the walls of the artery.

During this potentially lifesaving procedure, the doctor may insert a stent into the vessel at the site of the blockage. This small, typically metallic device helps to hold the vessel open and improves blood flow. This serves to relieve the symptoms of Coronary Artery Disease.

Unfortunately, stents do not provide an absolute solution to this problem. Restenosis, a narrowing of the passageway which may initiated by platelet adhesion and aggregation at the site of arterial injury, and thrombosis frequently occur at the site of the stent. "Thrombosis" describes the formation of a thrombus, or blood clot, inside a blood vessel. Thrombosis may be caused by the continuous stresses from blood flow over the stent. The longitudinal lumen of a stent usually, if not always, has an irregular surface or regions that protrude into the lumen that can produce a turbulent fluid flow. Alternatively, the thrombosis may be the result of a foreign body reaction to the stent. The formation of a blood clot within a blood vessel may cause tissue damage. Such a clot may be life threatening, particularly when it partially or completely blocks the flow of blood through a blood vessel. If thrombosis occurs as a result of the stent placement, a secondary procedure or a surgical bypass operation is required.

Products such as aspirin, dipyridamole and heparin are known in the art to dissolve such clots. While these products may eliminate the clot, they have the potential serious side effect of causing prolonged bleeding. Additionally, the effect of the administration of such products may only be reversed by the formation or addition of new platelets.

It is desired to be able to place a stent within a vessel through percutaneous transluminal delivery without the risk of in-stent thrombosis. Such stent placement without the risk of in-stent thrombosis would greatly increase the quality of life for many patients. Accordingly, a method to prevent the formation of in-stent thrombosis that is not detrimental to the patient is desired.

BRIEF DESCRIPTION OF THE DRAWINGS

FIG. 2(b) provides views of nitinol stents (side-on view) depicting thrombus burden under the various treatment conditions;

FIG. 4 provides a chart detailing experimental data collected from an experiment run in accordance with one embodiment of the present invention; and FIG. 5 provides a chart detailing the effects of the heparin and magnesium as used in an experiment according to one embodiment of the present invention on 5 µg/mL collagen-induced platelet aggregation, bleeding time and ACT.

DETAILED DESCRIPTION

Figure 1:
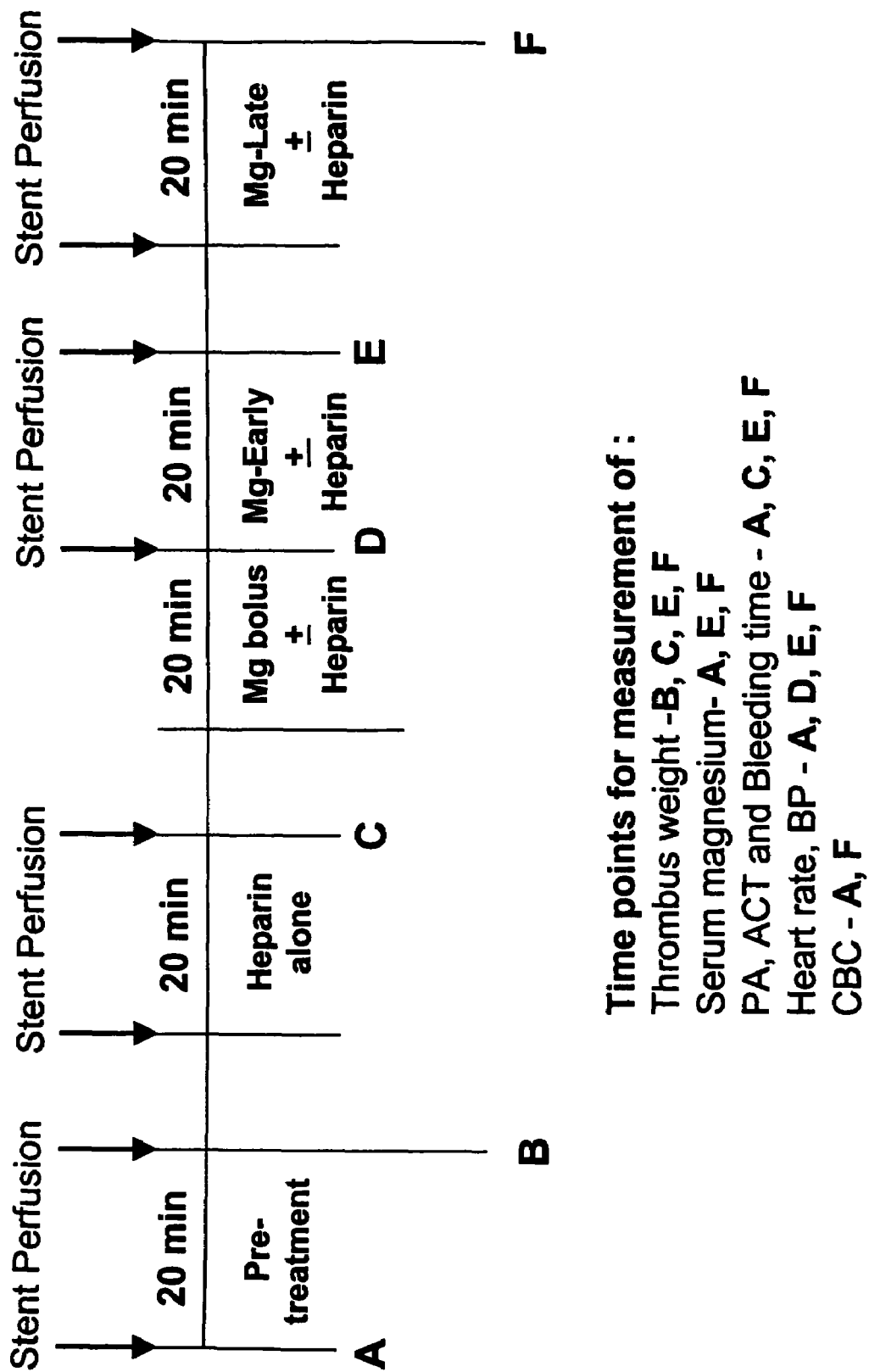
FIG. 1 illustrates a perfusion protocol that was run in an ex-vivo porcine shunt model according to an embodiment of the present.

The present invention is the discovery that the administration of magnesium produces a significant time-dependent inhibition, and potential prevention, of acute platelet-dependent stent thrombosis under high-shear flow conditions. This antithrombotic effect, which correlates directly with serum magnesium ion levels, is primarily due to the magnesium's effect on platelets, magnesium's effect on coagulation and fibrinolysis.

An additional feature of the present invention is that the inhibition of acute platelet-dependent stent thrombosis may be achieved without any hemostatic or significant hemodynamic complications. Importantly, a significant inhibition of platelet-thrombus formation was demonstrated with magnesium treatment without any effect on platelet aggregation or bleeding time. The potent antithrombotic effects of magnesium together with its safety, ease of administration, and low cost make it a promising treatment during percutaneous coronary intervention (PCI).

The timing of the magnesium administration according to the present invention is important to the inhibition of stent thrombosis. The maximum antithrombotic effect of Mg is evident when platelets are treated before exposure to thrombogenic stimuli. Such thrombogenic stimuli include, but are not limited to, catheters, endovascular devices, stent-bearing catheters, angioplasty, stents, laser catheters, atherectomy, radiation, extraction devices (for example: transluminal extraction atherectomy), angiojets, and local drug-delivery catheters.

This time-dependent effect may be seen in FIG. 4, which provides data from an experiment conducted in accordance with one embodiment of the present invention. As shown in FIG. 4, the antithrombotic effects of magnesium were significantly more pronounced when Mg was given 40 minutes, as opposed to 20 minutes, before initiation of stent perfusion. Given sufficient exposure to magnesium with appropriate timing, the administration of magnesium may be used to assist in the prevention of stent thrombosis.

The effects of the present invention are best seen when the magnesium is administered between about 30 and 60 minutes prior to thrombotic stimuli. However, it should be understood that the magnesium may be administered within a reasonable time outside of this range. For example, the magnesium may be administered between 15 and 90 minutes prior to thrombotic stimuli. The magnesium may be administered, at least in part, by coating a stent or other endoprosthesis with a magnesium-containing compound prior to insertion into a body passageway. Administration of the magnesium should be continued for approximately eight to twelve hours after the procedure.

In one embodiment of the present invention, magnesium is administered intravenously. Intravenous administration allows for greater control of the level of magnesium in the blood. As should be understood by one skilled in the art, however, the administration of magnesium is not limited to intravenous administration. Other methods of administration include, but are not limited to, oral ingestion and the administration of an injection. Oral administration of magnesium may be particularly beneficial to treat (or prevent) stent thrombosis in patients once they are discharged. The magnesium may alternatively be supplied to a patient through a catheter or other instrument which is inserted percutaneously, or through a tube attached to such instrument. Such an instrument may alternatively be coated with a magnesium-containing compound. In a further embodiment of the present invention, a stent may be coated with a magnesium-containing compound.

The use of magnesium disclosed herein has been thus far limited to a discussion of the inhibition of stent thrombosis. However, the present invention is not so limited. Magnesium may be administered as taught by the present invention to prevent thrombosis during angioplasty and bypass and other surgeries.

The magnesium may be administered in the form of magnesium sulfate ($MgSO_4$), or any other form of magnesium known by those skilled in the art to be non-toxic to the subject. Such non-toxic forms of magnesium include, but are not limited to, magnesium phosphate ($MgPO_4$), magnesium chloride (MgCl) and magnesium oxide (MgO).

Magnesium has an anti-adhesive effect on platelets that is achieved primarily by reducing calcium mobilization in platelets. It may also suppress fibrinogen interaction with platelets via competitive inhibition of calcium at the calcium-binding sites of the glycoprotein IIb-IIIa complex. See Gawaz M, Ott I, Reininger A J, Neumann F J. Effects of magnesium on platelet aggregation and adhesion: magnesium modulates surface expression of glycoproteins on platelets in vitro and ex vivo. Thromb Haemost, 1994; 72:912-918. The serum Mg levels achieved in the example discussed herein (3.7±0.3 for heparin+Mg-early and 3.8±0.4 for heparin+Mg-late) were in the range where the anti-adhesive effects would be more evident compared to the anti-aggregatory effect.

The discrepant effect on platelet adhesion/thrombus formation and platelet aggregation may relate to the fact that the anti-adhesive effect of Mg may occur at a lower concentration (<4 mEq/L) compared to the anti-aggregatory effect (>5 mEq/L). See Ravn H B, Kristensen S D, Hjortdal V E, Thygesen K, Husted S E, Early Administration of Intravenous Magnesium Inhibits Arterial Thrombus Formation, Arterioscler Thromb Vasc Biol, 1997; 17:3620-3625; and Gawaz M, Ott I, Reininger A J, Neumann F J, Effects of magnesium on platelet aggregation and adhesion: magnesium modulates surface expression of glycoproteins on platelets in vitro and ex vivo, Thromb Haemost, 1994; 72:912-918. Since the thrombus weights returned towards pre-treatment values during control perfusion runs post-treatment utilizing the same aortic strip, it is unlikely that the varying thrombogenicity of the porcine aortic strip may have contributed to treatment effect.

The role that magnesium may take in the treatment of cardiovascular diseases has not been determined. For example, recent clinical trials have presented conflicting evidence about the role of magnesium in acute myocardial infarction with the ISIS-4 trial (International Study of Infarct Survival) showing no benefit (ISIS-4: A randomized factorial trial assessing early oral captopril, oral mononitrate, and intravenous magnesium sulfate in 58,050 patients with suspected myocardial infarction. Lancet, 1995;345:669-685.) and the LIMIT-2 (Leicester Intravenous Magnesium Intervention Trial) study providing strong evidence for a survival advantage. See Woods K L, Fletcher S, Roffe C, Haider Y. Intravenous magnesium sulphate in suspected acute myocardial infarction: results of the second Leicester Intravenous Magnesium Intervention Trial (LIMIT-2). Lancet, 1992:339:1553-8.

Experimental Model

An experiment according to one embodiment of the present invention was performed using an ex-vivo model that primarily examines shear-mediated, platelet-dependent thrombus formation. This experiment allowed for the evaluation of the effects of magnesium, and the time-dependent nature thereof, on acute platelet-dependent stent thrombosis in an ex-vivo porcine arteriovenous shunt model of high-shear blood flow.

Such a model is useful to study interaction of blood elements with stents and thrombogenic surfaces under controlled and well-defined conditions. This ex-vivo system was chosen for its reproducibility and simplicity. It a sensitive tool to assess pre-clinical efficacy of antithrombotic therapeutic interventions.

Animal Surgery

All procedures of the animal surgery conducted in conjunction with the experiments discussed herein were performed in accordance with one embodiment of the present invention were approved by the Institutional Animal Care and Use Committee and conformed to the American Heart Association guidelines for animal research. Experiments were performed in 10 swine weighing 25 to 30 kg. After overnight fasting, swine were sedated with phenobarbital (5 mg/kg), and anesthesia was maintained with 1% isoflurane after endotracheal intubation. The right carotid artery and jugular vein were isolated and cannulated with 8F sheaths to establish an extracorporeal circuit as described previously. See Kaul S, Makkar R R, Nakamura M, Litvack F, Shah P K, Forrester J S, Hutsell T, Eigler N L, Inhibition of Acute Stent Thrombosis under High-Shear Flow Conditions by a Nitric Oxide Donor. DMHD/NO: An Ex-Vivo Porcine Arteriovenous Shunt Study, *Circulation*, 1996, 94:2228-34. Arterial blood gases and pH were monitored periodically and maintained at normal levels by adjustment of the ventilation rate and tidal volume. Invasive arterial pressure measurement, oxygen saturation, ECG, and rectal temperature were monitored continuously. A thermostatically controlled blanket was used to maintain temperature at 37° C. Venous blood was collected for baseline platelet aggregation, complete blood cell count, and activated clotting time (ACT) measurements.

All animals received heparin at a dose of 10 U/kg as a bolus before the study to prevent thrombotic occlusion of catheters and tubing. Each swine received an average of 200 U heparin, an amount that produces negligible effects on thrombus formation at high-shear conditions in this model. See Kaul S, Makkar R R, Nakamura M, Litvack F, Shah P K, Forrester J S, Hutsell T, Eigler N L, Inhibition of Acute Stent Thrombosis under High-Shear Flow Conditions by a Nitric Oxide Donor. DMHD/NO: An Ex-Vivo Porcine Arteriovenous Shunt Study. *Circulation*, 1996, 94:2228-34. At the conclusion of the experiment, blood was collected for complete blood cell counts, the carotid artery and jugular vein were ligated, and the animals were allowed to recover from anesthesia before being returned to the vivarium. Each animal was studied twice with a minimum interval of 2 weeks between each experiment.

Coronary Stents

The stents tested were 7-mm-long slotted-tube-geometry devices made from the nickel-titanium alloy NITINOL (Advanced Coronary Technology, Menlo Park, Calif.) (n=156 stents in 10 swine). Each stent weighed 24±3 mg and had a strut thickness of 0.006 in. They had a silicon carbide grit-blasted surface finish, which creates a uniform roughened surface known to be highly thrombogenic in this model. See Kaul S, Makkar R R, Nakamura M, Litvack F, Shah P K, Forrester J S, Hutsell T, Eigler N L, Inhibition of Acute Stent Thrombosis under High-Shear Flow Conditions by a Nitric Oxide Donor. DMHD/NO: An Ex-Vivo Porcine Arteriovenous Shunt Study. *Circulation*, 1996, 94:2228-34; and Makkar R R, Eigler N L, Kaul S, Nakamura M, Forrester J S, Herbert J-M, Litvack F I, Effects of clopidogrel, aspirin and combined therapy in a porcine ex vivo model of high-shear induced stent thrombosis, *Eur Heart J*, 1998; 19:1538-1546. Stents were expanded on a tapered mandrel to an open diameter of 2.0 mm before being mounted in the perfusion chamber.

Extracorporeal Shunt and Perfusion Protocol

The extracorporeal shunt system utilized in this study has been extensively characterized and described previously. See Kaul S, Makkar R R, Nakamura M, Litvack F, Shah P K, Forrester J S, Hutsell T, Eigler N L, Inhibition of Acute Stent Thrombosis under High-Shear Flow Conditions by a Nitric Oxide Donor. DMHD/NO: An Ex-Vivo Porcine Arteriovenous Shunt Study, *Circulation*, 1996, 94:2228-34; Makkar R R, Litvack F, Eigler N L, Nakamura M, Ivey P A, Forrester J S, Shah P K, Jordan R E, Kaul S, Effects of GP IIb/IIIa Receptor Monoclonal Antibody (7E3), Heparin, and Aspirin in an Ex Vivo Canine Arteriovenous Shunt Model of Stent Thrombosis, *Circulation*, 1997; 95(4): 1015-1021; and Makkar R R, Eigler N L, Kaul S, Nakamura M, Forrester J S, Herbert J-M, Litvack F I, Effects of clopidogrel, aspirin and combined therapy in a porcine ex vivo model of high-shear induced stent thrombosis, *Eur Heart J*, 1998; 19:1538-1546. After a 60-minute stabilization period, stents were mounted in the tubular chamber and perfused with normal saline for 60 seconds at 37° C. With a switch valve used to prevent stasis, blood was circulated through the system, and flow was regulated at 100 mL/min for 20 minutes by using a peristaltic pump (Masterflex, Cole-Palmer Instrument Co.) placed in the circuit distal to the perfusion chamber.

The selected flow rate generates a wall shear rate of 2100 $s^{-1}$ at the stent surface. Shear rates were calculated according to the formula for laminar flow of homogeneous Newtonian fluid in a cylindrical tube: shear rate=$4.Q/\pi \cdot R3$, where Q is volume flow and R is radius. See Goldsmith H L, Turitto V T, Rheological aspects of thrombosis and hemostasis: basic principles and applications, Thromb Haemost, 1986;55:415-435. At high shear rates, as used in this study, blood is considered to be essentially a Newtonian fluid.

At the end of the perfusion period, saline was circulated through the chamber and ex vivo system for several minutes at 40 mL/min to clear any visible blood before another stent was mounted. At the completion of each perfusion period, the stents (weighed prior to perfusion) were removed from the chamber, dried, and weighed immediately. Thrombus weight was calculated as a difference between pre- and post-perfusion stent weights.

The top of each stent was covered with a heterologous porcine aortic strip (Pel Freeze, Kans.) from which the intimal layer was removed to simulate the thrombogenic conditions induced by vascular injury associated with stent implantation. The number of stent perfusion runs examined varied from 6 to 8 during each experiment. Digital images of stents were obtained with a Nikon 950 digital camera, downloaded into a PC and processed with image analysis software (PhotoShop Adobe 5.0). A sample of such images may be seen in FIG. 2(b).

At the end of each treatment, control stents were perfused to ensure return of stent thrombus weights towards baseline pre-treatment values. Effects on thrombus weight (TW), whole-blood platelet aggregation (PA), bleeding time (BT), activated clotting time (ACT), serum magnesium level, and complete blood count (CBC) were quantified at various time points as shown in the protocol schematic. Mean arterial blood pressure (MABP) and heart rate (HR) were monitored and recorded throughout the protocol.

Thirty minutes after administration of the heparin (in the heparin alone) or magnesium, 3 mL venous blood was collected in a siliconized test tube containing 0.3 mL of 0.129 molar sodium citrate or sodium heparin (Becton Dickinson Vacutainer System). Whole blood aggregometry (Chronolog Corp.) was used to measure collagen (2 and 5 µg/mL)- and Adenosine diphosphate (2.5 µM)-induced platelet aggregation. Aggregation was expressed as maximal increase in electrical impedance measured in ohms at 6 minutes after the addition of agonist. The baseline platelet aggregation was 25±3 ohms. The platelet aggregation after the addition of Mg-late alone and heparin alone was 22±3 and 24±6 ohms, respectively. As noted above, data points in the Mg-treated animals were examined within 20 minutes post-bolus (Mg-early) and >40 minutes post-bolus (Mg-late). The platelet aggregation obtained within 20 minutes post-bolus was 23±4 ohms. The platelet aggregation obtained >40 minutes post-bolus was 21.0±5 ohms.

Bleeding time is defined as the time from the creation of an incision to the point where bleeding from the incision ceases. In the experiment according to one embodiment of the present invention discussed herein, bleeding time was measured from an incision on the ventral surface of the thigh with a No. 11 surgical knife.

In the experiment discussed herein that was conducted according to one embodiment of the present invention, ACT was determined using a Hemochron 400 (International Technidyne Corp.) machine in standard fashion. See Makkar R R, Litvack F, Eigler N L, Nakamura M, Ivey P A, Forrester J S, Shah P K, Jordan R E, Kaul S, Effects of GP IIb/IIIa Receptor Monoclonal Antibody (7E3), Heparin, and Aspirin in an Ex Vivo Canine Arteriovenous Shunt Model of Stent Thrombosis, Circulation, 1997; 95(4): 1015-1021; and Makkar R R, Eigler N L, Kaul S, Nakamura M, Forrester J S, Herbert J-M, Litvack F I, Effects of clopidogrel, aspirin and combined therapy in a porcine ex vivo model of high-shear induced stent thrombosis, Eur Heart J, 1998; 19:1538-1546.

Serum magnesium levels for the test subjects were measured spectrophotometrically using the magon dye method. See Elm R J, Determination of serum magnesium concentration by clinical laboratories, *Magnes Trace Elem*, 1991- 92:60-6.

FIG. 1 illustrates a perfusion protocol that was run in an ex-vivo porcine shunt model according to an embodiment of the present invention. As used in FIG. 1, PA means platelet aggregation, ACT means activated clotting time, BP means arterial blood pressure, and CBC means complete blood count. In order to obtain control thrombus weight, two to three stents were perfused in each animal prior to the administration of any drug.

The stents were perfused pre- and post-treatment with heparin or magnesium in a random fashion. Heparin was administered as 50 U/kg IV bolus followed by 25-50 U/kg/hr IV to keep ACT >150 seconds. Magnesium sulfate (MgSO4) was administered as a 2 gm bolus IV over 20 minutes followed by 2 gm/hour maintenance infusion. To assess a potential time-dependent antithrombotic effect of magnesium, data points were examined within 20 minutes post-bolus (Mg-early) and >40 minutes post-bolus (Mg-late). The time-dependent effects of magnesium were also examined in a random fashion.

As shown in FIG. 1, the "pre-treatment" readings were taken from a stent that was expanded to 2 mm in diameter in a tubular perfusion chamber interposed in the shunt and perfused with blood at a shear rate of 2100 s$^{-1}$ for 20 minutes, without any magnesium or heparin in the system. The "heparin alone" readings were taken from stents that were perfused with blood for 20 minutes when the animals had been treated with intravenous heparin as described above. The perfusion study for the "heparin alone" reading was performed between twenty and thirty minutes after the administration of heparin. Both the "heparin+Mg-Early" and "heparin+Mg-Late" readings were taken from stents that were perfused with blood for 20 minutes after the animals had been treated with intravenous heparin and magnesium as noted above. The perfusion period for the heparin+Mg-early readings started within 20 minutes after administration of the MgSO$_4$ bolus. The perfusion period for the heparin +Mg-late readings started more than 40 minutes after the administration of the MgSO$_4$ bolus.

In one embodiment of the present invention, the magnesium bolus is followed by a 1 to 2 gm/hour maintenance infusion. For example, in the experiment discussed in FIG. 1 herein, a 2 gm bolus IV was administered to the test subject over 20 minutes followed by a 2 gm/hour maintenance infusion for an average magnesium dosage of 9 gm in a 30-kg pig (the dosages ranged from 5-13 gm).

The magnesium dosage required to achieve the benefits of one embodiment of the present invention is generally between 0.16 gm and 0.4 gm per kilogram body weight. A human weighing 100-kg would preferably intravenously receive an approximately 2 gm bolus IV for roughly 10-20 minutes. This would preferably be followed by an approximately 2 gm/hour maintenance infusion for roughly 8-12 hours. It should be understood by one skilled in the art, however, that these dosages and times of administration may be varied depending on a number of factors including, but not limited to, the size of the subject. That is, a bolus dose of 1-4 gm over 10-20 minutes may be administered, followed by a maintenance dose of 1-4 gm/hr. It should be noted that at higher bolus and maintenance doses greater anti-thrombotic effects are observed. However, higher dosages also tend to affect heart rate and blood pressure.

Figure 2A:
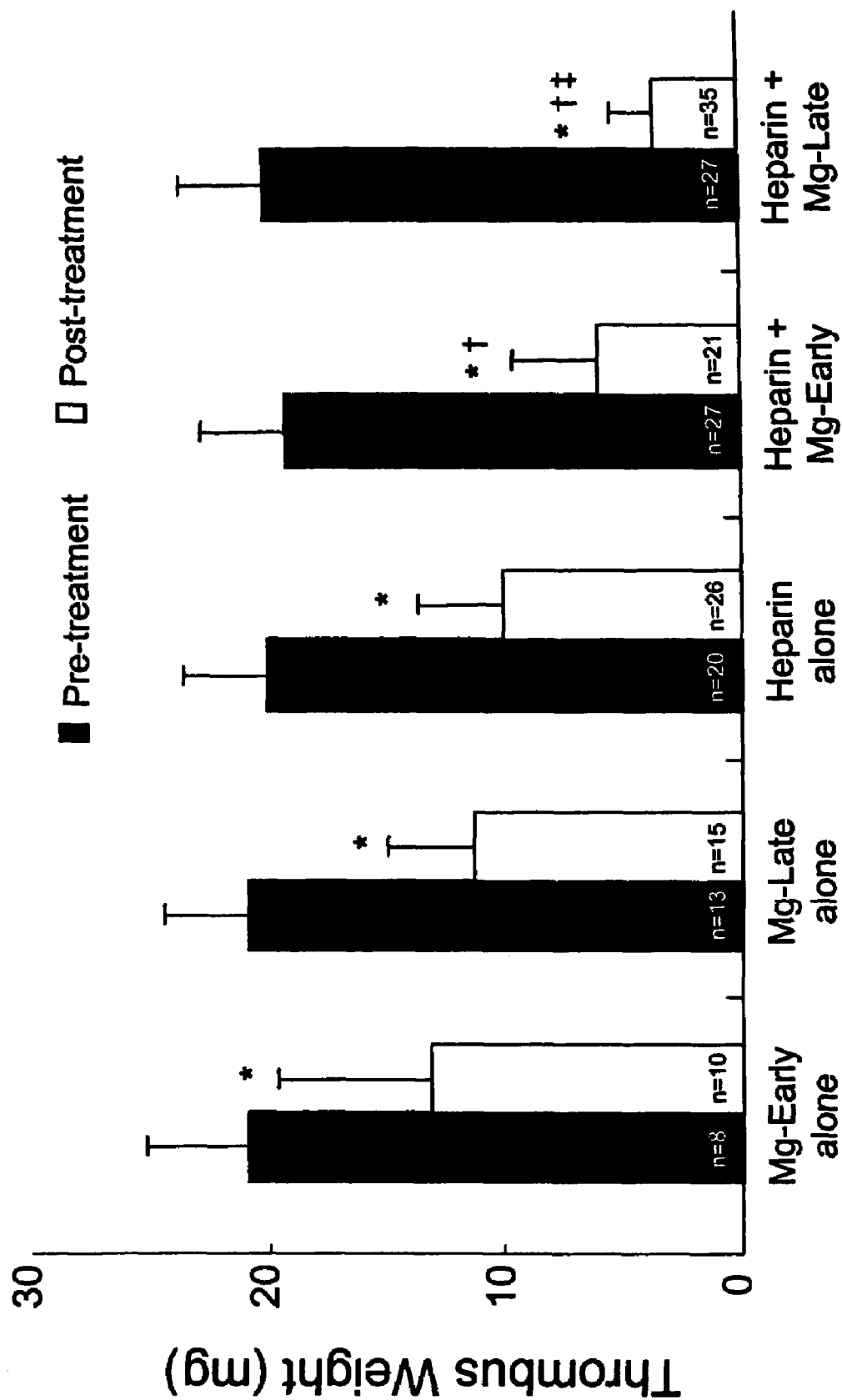
FIG. 2(a) provides bar graphs showing the effect on thrombus weight in different treatment groups in an experiment according to one embodiment of the present invention.

FIG. 2(a) provides a bar graph showing the effect on thrombus weight in different treatment groups in an experiment according to one embodiment of the present invention. FIG. 2(b) provides side-on views of nitinol stents depicting thrombus burden under the various treatment conditions. Values are given as mean±SD. Eight to 15 stents were tested in the Magnesium alone groups. The number of stents varied between 20 and 35.

As may be seen from FIG. 2(a), the category of stents labeled "pre-treatment" has the greatest amount of stent thrombosis. Magnesium alone (both early and late groups) as well as heparin reduce thrombus formation slightly. Heparin with magnesium-early reduces the thrombosis more significantly, and heparin with magnesium-late virtually prevented thrombus formation.

Figure 3:
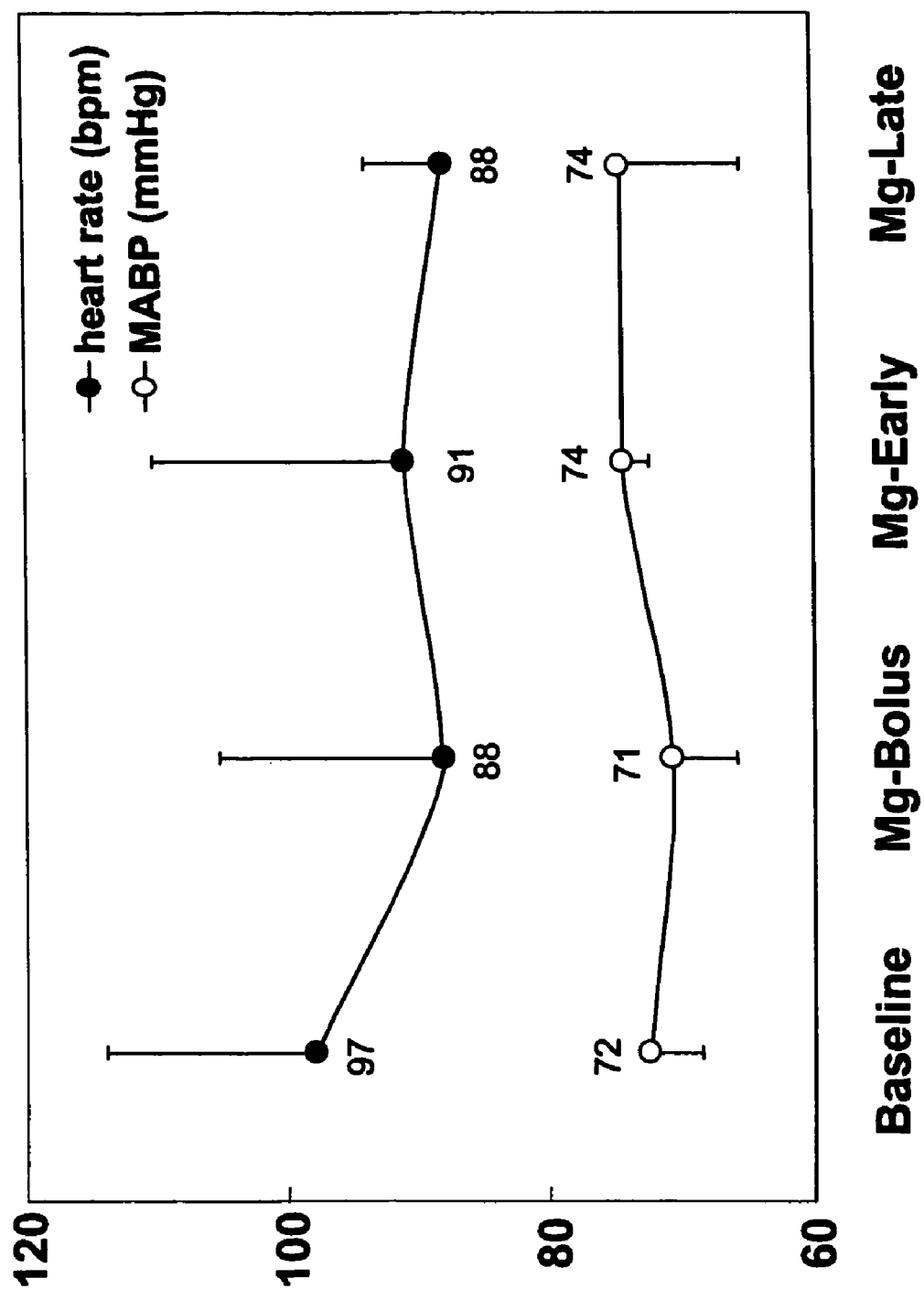
FIG. 3 provides a graphical depiction of the effects of magnesium on heart rate and mean arterial blood pressure as shown by an experiment that was conducted according to one embodiment of the present invention.

FIG. 3 provides a graphical depiction of the effects according to one embodiment of the present invention of magnesium on heart rate and mean arterial blood pressure (MABP). In this experiment, magnesium in the form of magnesium sulfate was administered intravenously to the subject animals. Values are again provided as mean±SD. As may be seen from FIG. 3, magnesium had no statistically significant effects on either heart rate or MABP.

The graph in FIG. 3 was generated by taking between 10 and 14 observations at each time point. The MABP was measured in millimeters of mercury (mmHg). The heart rate was measured in beats per minute (BPM). As may be seen from the graph, no statistically significant changes in heart rate and blood pressure were observed using ANOVA.

FIG. 4 provides a chart detailing the reduction in stent thrombosis based on five differing stimuli according to one embodiment of the present invention. Particularly, FIG. 4 shows the effects of treatment with magnesium alone, heparin alone as well as combined treatment with magnesium and heparin on acute stent thrombosis. The data shown in FIG. 4 was obtained from an experiment similar to that which was discussed in FIGS. 2(a) and (b).

The total weight of a stent that was perfused with blood without the addition of heparin or magnesium was 20±4 mg is referred to as stent TW. As shown in FIG. 1, the "pre-treatment," or baseline stent TW, readings were taken from a stent that was perfused with blood for 20 minutes, without any magnesium or heparin in the system. This number was used to calculate the reduction in thrombus formation. The reduction in thrombus formation was calculated by subtracting the weight of a post-treatment stent (post-heparin or magnesium treatment) from the average weight of a stent that had been perfused with blood without the addition of heparin or magnesium.

As shown in FIG. 4, stent TW was reduced by 42±21%, 47±19%, 48±16% in the Mg-early, Mg-late and heparin-treated group, respectively. The weight was reduced by 67±12% in the heparin+Mg-early-treated group. The thrombus weight was further reduced by 86±8% in the heparin+Mg-late-treated group. All five of these calculations had a P<0.001 versus pretreatment. (P<0.05 heparin+Mg-late versus heparin and Mg-early; P<0.01 heparin+Mg-early and Mg-late versus heparin alone, Mg-early and late alone, ANOVA). Magnesium had no significant effects on platelet aggregation, activated clotting time and bleeding time. The serum Mg level was the only variable that correlated with TW (r=−0.70. P.002). There were no significant effects on heart rate or mean arterial blood pressure.

As may be seen in FIG. 4, the antithrombotic effects of combined treatment with heparin and Mg were significantly more pronounced compared with magnesium or heparin alone (P<.001, ANOVA). Heparin+Mg-late produced a slightly greater, and statistically significant, reduction in TW compared with heparin+Mg-early group (P<0.05, ANOVA).

FIG. 5 provides a chart detailing the effects of the heparin and magnesium as used in an experiment according to one embodiment of the present invention on 5 μg/mL collagen-induced platelet aggregation, bleeding time and ACTs.

As shown in FIG. 5, the reduction in whole-blood platelet aggregation with the addition of magnesium, from 25±3 to 21±5 ohms, was not significant. To exclude the possibility that minimal magnesium effect on platelet aggregation may be related to the citrate anticoagulant used which may influence ionic concentrations because of calcium chelation in the samples, aggregation was tested in heparinized as well as citrated blood in 3 pigs. Magnesium produced no significant inhibitory effect on platelet aggregation in heparin-stabilized samples (26±2 pre- and 27±2 post-Mg) as compared to citrate-stabilized blood (25±3 pre- and 22±3 post-Mg). Platelet aggregation was, however, slightly enhanced in heparinized samples. There was no effect of magnesium on platelet aggregation in response to either a lower concentration of collagen-2 μg/ml or to another platelet agonist—ADP (2.5 μM) (data not shown). Therefore, magnesium had no significant effect on platelet aggregation, regardless of the anticoagulant used to stabilize blood.

As shown in FIG. 5, heparin increased the bleeding time from 4.0±0.5 to 5.3±0.6. Heparin also prolonged ACT from 109±8 seconds to 185±36 seconds (P<0.01. ANOVA). Magnesium had no significant effects on either bleeding time or ACT beyond the heparin effect. There were no episodes of significant bleeding in any of the animals studied. Treatment with heparin or magnesium had no significant effects on either platelet or white blood cell counts or hematocrit (data not shown).

As further shown in FIG. 5, serum magnesium levels were higher in the magnesium-treated animals compared to control. However, the levels were virtually similar in the Mg-early and Mg-late group. Serum magnesium correlates significantly with thrombus weight (r=−0.70. P=0.002), bleeding time (r=0.54, P=0.05) and heart rate (r=−0.55, P=0.002). Serum magnesium was the only variable that correlated significantly with thrombus weigh. No significant correlation of thrombus weight was observed with platelet aggregation (r=0.4, P=0.07).

As previously noted, the timing of the administration of magnesium weighs significantly on the benefit seen in reduced thrombosis weight. Heparin+Mg-early produced a significant reduction in thrombosis weight when compared to the thrombus weight for heparin alone or the pre-treatment group. However, heparin+Mg-late produced an even greater reduction in thrombosis weight. The difference in antithrombotic effect in Mg-early and Mg-late group cannot be solely explained by a dose-dependent effect since serum magnesium levels were not significantly different. However, serum magnesium does not accurately reflect intracellular levels of magnesium. Given the increased exposure to magnesium, it is likely that the intracellular levels of Mg may be higher in the Mg-late as compared with Mg-early tests despite similar serum Mg levels.

Human Testing

One embodiment of the present invention was tested in human subjects, with very positive results. Based on these tests, the use of magnesium was determined to be beneficial to prevent in-stent thrombosis. This effect was evident without any hemostatic or hemodynamic complications.

Twenty one low-risk patients undergoing non-acute percutaneous coronary intervention with stent implantation received a two gm bolus of intravenous $MgSO_4$ followed by a 1.5 gm/hour infusion for four hours and a 1 gm/hour infusion for the next eight hours. This test resulted in a total administration of 16 gm of magnesium. The preset primary endpoints for this experiment were: acute thrombotic occlusion and need for platelet IIb/IIIa inhibitors bailout, death, myocardial infarction, recurrent ischemia and need for urgent revascularization at 48 hours and 30 days. The secondary safety endpoints included hypotension, bradycardia, bleeding complications and heart block within the first 24 hours.

In all cases, the interventions were finished with normal coronary artery blood flow (TIMI 3 flow). There was no case of GP IIb/IIIa inhibitors bailout. Death, myocardial infarction, and urgent revascularization were also not seen. Serum magnesium levels increased significantly from a 2.1±0.3 baseline to 3.2±0.3 mg/dL post-bolus (P<0.0001). Further, magnesium did not have a significant effect on either heart rate or mean arterial blood pressure. There was no further significant increase in magnesium concentration after completion of the magnesium sulfate infusion (the magnesium level post-infusion was 3.5±0.8 mg/dL).

All of the data presented herein is presented as mean±SD. The statistical difference between means was determined by one-way ANOVA. If means were shown to be significantly different, multiple comparisons by pairs were performed by the Bonferroni test (Graphpad Prism version 3.0). Spearman's correlation analysis was performed to explore the relationship between serum magnesium and other variables and between thrombus size and other variables. A value of P<0.05 was considered significant.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. A method of reducing stent thrombosis under high shear blood flow conditions in a subject, the method comprising:
    providing a stent coated with an effective amount of a magnesium-based compound to administer the magnesium-based compound; and
    inserting the stent within a body passageway in the subject.

2. The method of claim 1, wherein the magnesium-based compound is selected from the group consisting of magnesium sulfate, magnesium oxide, magnesium phosphate, and magnesium chloride.

3. The method of claim 1, further including the step of associating the stent with an instrument for inserting the stent within a body passageway.

4. The method of claim 3, wherein the instrument is coated with a magnesium-containing compound to administer the magnesium-based compound.

5. The method of claim 1, further including the step of administering a magnesium-based compound to a subject so that a serum magnesium level between 3 and 5 mEq/L is attained prior to exposure of the subject to a stent-induced thrombogenic stimuli, wherein the administering step is carried out prior to inserting the stent within the body passageway.

6. The method of reducing stent thrombosis according to claim 5, wherein the serum magnesium level is attained at least 15-20 minutes before the subject is exposed to the stent-induced thrombogenic stimuli.

7. The method of claim 1, further comprising administering an effective amount of a magnesium-based compound to the subject between approximately 15 and 90 minutes prior to insertion of the stent.

8. The method of claim 7, wherein the magnesium-based compound coated on the stent and the further administered magnesium-based compound are selected from the group consisting of magnesium sulfate, magnesium oxide, magnesium phosphate, and magnesium chloride.

9. The method of claim 7, wherein the magnesium-based compound is administered intravenously.

10. The method of claim 7, wherein the magnesium-based compound is administered as an injection.

11. The method of claim 7, wherein the magnesium-based compound is administered to the subject between 30 and 60 minutes prior to insertion of the stent.

12. The method of claim 7, further comprising administering an effective amount of heparin to the subject.

13. The method of claim 7, wherein administering an effective amount of a magnesium-based compound comprises administering the magnesium-based compound as a 2 gm bolus.

14. The method of claim 13, wherein the bolus is administered over a 10 to 20 minute time period.

15. The method of claim 13, wherein after administering the magnesium-based compound as a 2 gm bolus, the method further comprises administering a 1 to 1.5 gm/hour maintenance infusion of a maintenance magnesium-based compound.

16. The method of claim 15, wherein the maintenance infusion is administered after inserting the stent into the subject.

17. The method of claim 15, wherein the maintenance infusion is administered over an 8 to 12 hour time period.

18. The method of claim 15, wherein the maintenance magnesium-based compound is selected from the group consisting of magnesium sulfate, magnesium oxide, magnesium phosphate, and magnesium chloride.

19. The method of reducing stent thrombosis according to claim 6, wherein the further administered magnesium-based compound is administered intravenously.

20. A method of reducing stent thrombosis under high shear blood flow conditions in a subject, the method comprising:
administering a magnesium-based compound intravenously to a subject so that a serum magnesium level between 3 and 5 mEq/L is attained prior to exposure of the subject to a stent-induced thrombogenic stimuli, wherein the administering step is carried out prior to inserting the stent within the body passageway;
providing a stent coated with an effective amount of a magnesium-based compound selected from the group consisting of magnesium sulfate, magnesium oxide, magnesium phosphate, and magnesium chloride;
associating the stent with an instrument coated with a magnesium-containing compound for inserting the stent within a body passageway; and
inserting the stent within a body passageway in the subject.

21. The method of reducing stent thrombosis according to claim 20, wherein the serum magnesium level is attained at least 15-20 minutes before the subject is exposed to the stent-induced thrombogenic stimuli.

22. A method of reducing stent thrombosis under high shear blood flow conditions in a subject, the method comprising:
providing a stent coated with an effective amount of a magnesium-based compound;
inserting the stent within a body passageway in the subject; and
administering an effective amount of a magnesium-based compound to the subject between approximately 15 and 90 minutes prior to insertion of the stent.

23. The method of claim 22, wherein the magnesium-based compound coated on the stent and the magnesium-based compound administered prior to insertion of the stent are selected from the group consisting of magnesium sulfate, magnesium oxide, magnesium phosphate, and magnesium chloride.

24. The method of claim 22, wherein the magnesium-based compound administered prior to insertion of the stent is administered intravenously.

25. The method of claim 22, wherein the magnesium-based compound administered prior to insertion of the stent is administered as an injection.

26. The method of claim 22, wherein the magnesium-based compound administered prior to insertion of the stent is administered to the subject between 30 and 60 minutes prior to insertion of the stent.

27. The method of claim 22, further comprising administering an effective amount of heparin to the subject.

28. The method of claim 22, wherein administering an effective amount of a magnesium-based compound comprises administering the magnesium-based compound as a 2 gm bolus.

29. The method of claim 28, wherein the bolus is administered over a 10 to 20 minute time period.

30. The method of claim 28, wherein after administering the magnesium-based compound as a 2 gm bolus, the method further comprises administering a 1 to 1.5 gm/hour maintenance infusion of a maintenance magnesium-based compound.

31. The method of claim 30, wherein the maintenance infusion is administered after inserting the stent into the subject.

32. The method of claim 30, wherein the maintenance infusion is administered over an 8 to 12 hour time period.

33. The method of claim 30, wherein the maintenance magnesium-based compound is selected from the group consisting of magnesium sulfate, magnesium oxide, magnesium phosphate, and magnesium chloride.

* * * * *